United States Patent [19]
Frisbie et al.

[11] Patent Number: 4,730,616
[45] Date of Patent: Mar. 15, 1988

[54] MULTIPLE PROBE ANGIOPLASTY APPARATUS AND METHOD

[75] Inventors: Jeffrey S. Frisbie, San Jose; Wilfred J. Samson, Saratoga, both of Calif.

[73] Assignee: Advanced Cardiovascular Systems, Inc., Mountain View, Calif.

[21] Appl. No.: 848,776

[22] Filed: Apr. 7, 1986

Related U.S. Application Data

[63] Continuation-in-part of Ser. No. 522,835, Aug. 12, 1983, Pat. No. 4,582,181.

[51] Int. Cl.⁴ ............................................. A61M 25/00
[52] U.S. Cl. .................................. 128/348.1; 604/164
[58] Field of Search ..................... 128/348.1; 604/164, 604/165, 270–273

[56] References Cited

U.S. PATENT DOCUMENTS 4,016,879  4/1977  Mellor ............................... 604/164
4,604,094  8/1986  Shook ............................... 128/348.1
4,619,643  10/1986  Liang Bai ........................... 604/164

Primary Examiner—Robert Peshock
Attorney, Agent, or Firm—Fulwider, Patton, Rieber, Lee & Utecht

[57] ABSTRACT

Hemostatic valve and method for positioning a plurality of elongated elements such as dilatation catheters and guide wires in the cardiovascular system. The hemostatic valve has two or more separately sealable access ports through which the elongated elements can be inserted and manipulated independently of each other.

17 Claims, 8 Drawing Figures

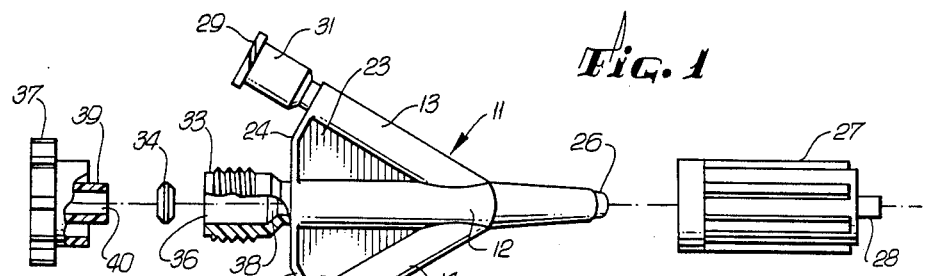
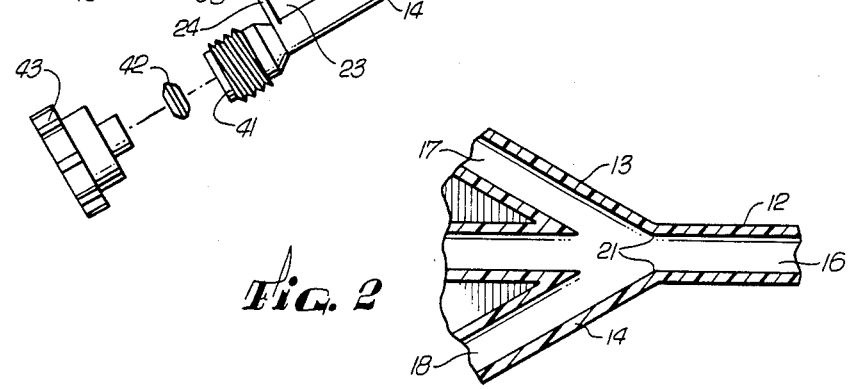
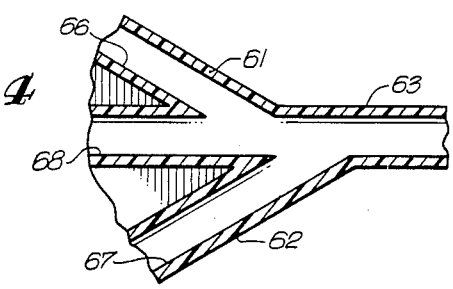
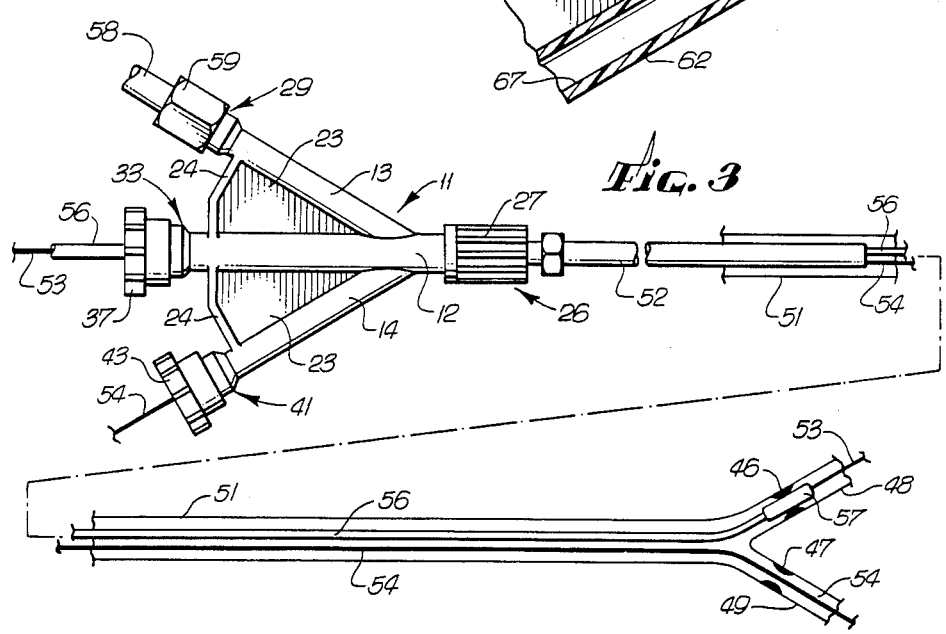

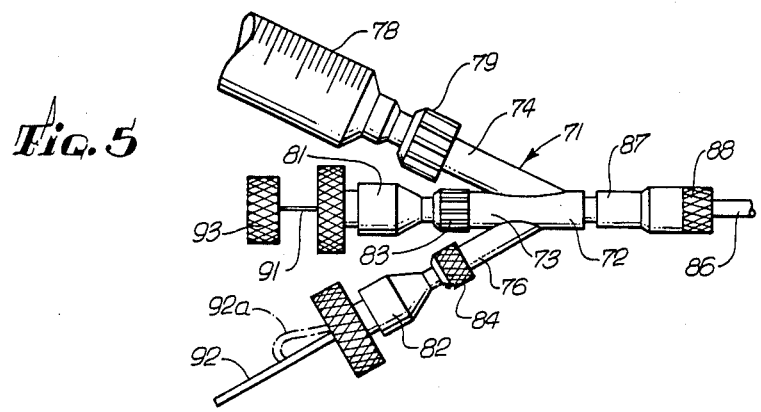
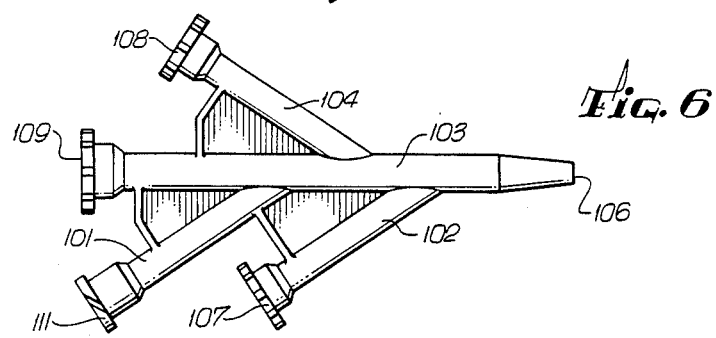
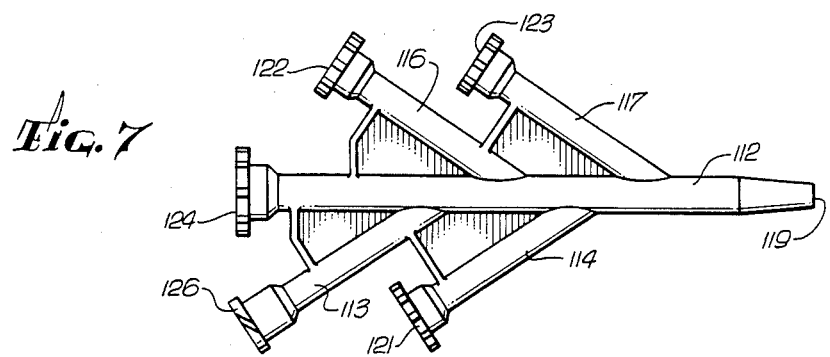
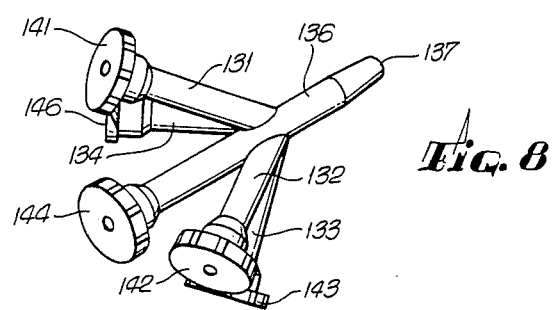

MULTIPLE PROBE ANGIOPLASTY APPARATUS AND METHOD

This is a continuation-in-part of Ser. No. 522,835, filed Aug. 12, 1983, in the name of Wilfred J. Samson, now U.S. Pat. No. 4,582,181, Apr. 15, 1986.

This invention pertains generally to coronary angioplasty, and more particularly to apparatus and a method for positioning a plurality of elongated elements in the cardiovascular system.

In percutaneous transluminal coronary angioplasty, catheters are inserted into the cardiovascular system through the femoral or brachial arteries under local anesthesia. A preshaped guiding catheter is positioned in the coronary artery, and a dilatation catheter having a distensible balloon portion is advanced through this catheter into the branches of the coronary artery until the balloon portion traverses or crosses a stenotic lesion. The balloon portion is then inflated with a fluid to compress the atherosclerosis in a direction generally perpendicular to the wall of the artery, thereby dilating the lumen of the artery.

A guide wire is often employed to facilitate placement of the dilatation catheter beyond the distal end of the guiding catheter. The guide wire is inserted through the guiding catheter, and the dilatation catheter is advanced along the guide wire to the desired position in the vascular system.

In some procedures, it is desirable to utilize more than one dilatation catheter and/or guide wire at a time. In one such procedure, for example, dilatation catheters are positioned adjacent to separate lesions and inflated to dilate the two lesions either simultaneously or in sequence. Another instance in which the use of two dilatation catheters is desirable is when a lesion is located near or involves a branch of two vessels and there is a possibility that dilation of one branch will cause the other to close off or occlude. To prevent such closure, or to treat it if it occurs, a second dilatation catheter can be inserted into the branch not being immediately treated. In the event that the luminal opening of the guiding catheter is not large enough to accommodate the two dilatation catheters at the same time, a guide wire is positioned in the branch not being immediately treated so that the second dilatation catheter can be advanced along the wire and positioned quickly if the need should arise. In these procedures, it is essential that the two guide wires and the two dilatation catheters be movable freely and independently of each other.

At times, it may be desirable to use three or more elongated elements, such as a dilatation catheter and two guide wires in a procedure at a vessel trifurcation, or a dilatation probe, a guide wire and a velocity probe, for example.

To control hemostasis, guide wires and catheters have been introduced into the body through a hemostatic valve. The hemostatic valves heretofore provided have had only one access port through which the guide wires and catheters can be introduced. When more than one guide wire or catheter is employed, it is virtually impossible to move them independently in a single access port. The port is sealed, and it is necessary to loosen the seal in order to move the element(s) passing therethrough. When more than one guide wire or catheter is employed, loosening the seal for one also loosens the seal for the other(s).

It is in general an object of the invention to provide a new and improved hemostatic valve and method for positioning elements in the cardiovascular system.

Another object of the invention is to provide a hemostatic valve and method of the above character which permit a plurality of guide wires and/or dilatation catheters to be manipulated and positioned independently of each other.

Another object of the invention is to provide a hemostatic valve and method of the above character in which a separate seal is provided for each of the elements.

These and other objects are achieved in accordance with one embodiment of the invention by providing a hemostatic valve having an exit port adapted for connection to a guiding catheter or the like, an instrumentation port in fluid communication with the exit port, a first sealable access port adapted to receive a first elongated element which passes through the guiding catheter, and a second access port sealable independently of the first access port for receiving a second elongated element which passes through the guiding catheter and can be manipulated independently of the first element. In other embodiments, additional access ports are provided for receiving three or more elongated elements, each of which is undependently movable and separately sealed.

FIG. 1 is an exploded elevational view of one embodiment of a hemostatic valve according to the invention.

FIG. 2 is an enlarged fragmentary sectional view of a portion of the hemostatic valve of FIG. 1.

FIG. 3 is a schematic view illustrating the use of the hemostatic valve of FIG. 1 with a plurality of elongated probes to dilate lesions on opposite sides of a bifurcation in the vascular system.

FIG. 4 is a view similar to FIG. 2 of a modified embodiment of a hemostatic valve according to the invention.

FIG. 5 is an elevational view of another embodiment of apparatus according to the invention.

FIGS. 6 and 7 are side elevational views of additional embodiments of hemostatic valves according to the invention.

FIG. 8 is an isometric view of another embodiment of another hemostatic valve according to the invention.

As illustrated in FIGS. 1 and 2, the hemostatic valve comprises a body 11 having a central arm 12 and a pair of side arms 13, 14 in which passageways 16, 17 and 18 are formed. The side arms extend at an angle relative to the central arm and intersect the central arm near its distal end, with passageways 17, 18 intersecting passageway 16 at the junction of the arms. The side arms flank the central arm in a common plane, and passageways 17, 18 intersect the distal end of passageway 16 at an obtuse angle which permits a smooth transition between these portions of the passageways. If desired, the corners or points 21 between the intersecting passageways can be rounded to provide an even smoother transition. Generally triangular gusset plates 23 extend between the central arm and the two side arms, with flanges 24 along the free edges of the gusset plates.

An exit port 26 is formed at the distal end of passageway 16 for connection to a guiding catheter (not shown) or the like, and means is provided for rotatively connecting the guiding catheter to the exit port. This means comprises a rotator 27 which is mounted on the distal end portion of the central arm and has a male Luer fitting 28 for connection to a corresponding connector at the proximal end of the guiding catheter. The rotator can be of a suitable known design, and it maintains a fluid-tight seal while permitting the Luer fitting to rotate about the axis of the central arm. If rotational capability is not desired, the rotator can be omitted and a stationary connector can be affixed to the distal end of the central arm.

An instrumentation port 29 is provided at the distal end of side arm 13 in fluid communication with exit port 26 through passageways 17 and 16. Means is provided for connecting this port to instrumentation such as a pressure monitor or a source of pressurized fluid. In the embodiment illustrated, this means comprises a female Luer fitting 31 which is formed as an integral part of side arm 13.

A first access port 33 is formed at the proximal end of central arm 12 in axial alignment with exit port 26 for receiving an elongated element such as a guide wire or a dilatation catheter (not shown). Means is provided for sealing the access port to control hemostasis. This means includes a sealing ring or gland 34 mounted in a bore 36 of enlarged diameter at the proximal end of passageway 16 and an end cap 37 threadedly mounted on the distal end of central arm 12. A radially extending shoulder 38 forms a seat for the sealing gland at the inner end of the bore, and in the embodiment illustrated, this seat is conically tapered. The end cap has an axially extending stem or post 39 which engages the sealing gland and compresses against the seat as the cap is tightened. The elongated element passes through an axial opening 40 in the end cap, and compression of the sealing gland forms a fluid-tight seal between this element and the valve body.

A second access port 41 is formed in side arm 14 for receiving a second elongated element. This port is similar to the first access port, but it is separately sealed, and elements inserted into the two ports can be manipulated and positioned independently of each other. Port 41 includes a bore and seat (not shown) similar to bore 36 and seat 38, a sealing gland 42 similar to sealing gland 34, and an end cap 43 similar to end cap 37.

Operation and use of the hemostatic valve, and therein the method of the invention, are illustrated in FIG. 3. In this embodiment, the obstruction to be cleared comprises lesions 46, 47 in the two branches 48, 49 of a bifurcation in the left anterior descending artery (LAD) 51. A guiding catheter 52 is connected to exit port 26 and advanced to the osteum of the heart. A guide wire 53 is inserted into the guiding catheter through access port 33 and advanced down the LAD across lesion 46 in branch 48 of the bifurcation. A second guide wire 54 is inserted into the guiding catheter through access port 41 and advanced down the LAD across lesion 47 in branch 49. End caps 37, 43 are tightened to compress sealing glands 34, 42 and form fluid-tight seals about the respective guide wires. The two guide wires can be moved and positioned independently of each other, and either end cap can be loosened to permit movement of a guide wire without disturbing the seal for the other guide wire.

A dilatation catheter 56 is inserted over the guide wire 53, through access port 33 and advanced along guide wire 53 until the balloon portion 57 of the catheter crosses lesion 46. End cap 37 is adjusted to provide a fluidtight seal about the catheter, and the balloon is inflated to dilate the lesion. If the guiding catheter is large enough, a second dilatation catheter (not shown) can be inserted through access port 41 and advanced along guide wire 54 to dilate lesion 47 simultaneously with the dilation of lesion 46. Otherwise, dilatation catheter 56 is removed after the first lesion is dilated, and the second dilatation catheter is then inserted over guide wire 54 to dilate the second lesion. With guide wire 54 already in position, the second dilatation catheter can be positioned quickly in the event of a spontaneous occlusion of lesion 47 while lesion 46 is being dilated.

Instrumentation port 29 is connected to the desired instrumentation by a line 58 having a connector 59 which mates with Luer fitting 31. In one presently preferred embodiment, the instrumentation port is connected to a manifold (not shown) to which a source of pressurized fluid and a pressure monitor are also connected.

The modified embodiment illustrated in FIG. 4 is similar to the embodiment of FIGS. 1-2 except the two side arms 61, 62 are offset longitudinally along central arm 63 so that side arm passageways 66, 67 are not directly opposite each other where they intersect passageway 68 in the central arm. Even with the passageways directly opposite each other, as in the embodiment of FIGS. 1-2, there is little chance that an element inserted in one of the passageways will inadvertently enter the other. However, with the passageways offset, the possibility of an element inadvertently entering passageway 66 from passageway 67 is even more remote.

The valve assembly can be fabricated of any suitable material such as a suitable plastic, and it can be formed by a suitable process such as molding.

The apparatus illustrated in FIG. 5 includes a three-arm adapter 71 having a body portion 72 with a central arm 73 and side arms 74, 76. A syringe 78 for injecting pressurized fluids is connected to side arm 74 by a connector 79, and the proximal ends of the passageways in central arm 73 and side arm 76 are sealed by valve assemblies 81, 82 similar to the means by which access ports 33, 41 are sealed in the embodiment of FIGS. 1-2. The valve assemblies are connected to the adapter arms by connectors 83, 84.

The tubular body of a catheter 86 is connected to the distal end of central arm 73 by connectors 87, 88, a first elongated element 91 passes through valve assembly 81 into this catheter, and a second elongated element 92 passes through valve assembly 82 to the catheter. A control knob 93 is connected to the proximal end of element 91 to aid in steering this element during placement in the cardiovascular system. Elements 91, 92 are separately sealed by valve assemblies 81, 82, and element 92 can be manipulated and positioned independently of element 91.

Catheter 86 and elements 91, 92 can be any suitable elements for insertion into the cardiovascular system. Catheter 86 can be a guiding catheter, and elements 91, 92 can, for example, be guide wires and dilatation catheters as discussed above. In the embodiment disclosed in Ser. No. 522,835, catheter 86 is a dilatation catheter, element 91 is a guide wire to which the distal end of the catheter is sealed, and element 92 is a vent tube which is inserted into the balloon portion of the catheter to remove trapped air. The proximal end portion of the vent tube can be folded back on itself and sealed by valve assembly 82, as indicated by dotted line 92a.

The embodiments illustrated in FIGS. 6 and 7 are generally similar to the embodiments of FIGS. 1 and 2, with additional access ports for receiving additional elongated elements. The embodiment of FIG. 6 has three separately sealable access ports, and the embodiment of FIG. 7 has four.

In the embodiment of FIG. 6, the hemostatic valve has two side arms 101, 102 on one side of a central arm 103 and one side arm 104 on the other side. An exit port 106 is provided at the distal end of the central arm, and access ports 107-109 are provided at the proximal ends of side arms 102, 104 and central arm 103. An instrumentation port 111 is provided at the proximal end of side arm 101. Each of the access ports is separately sealable and similar to access ports 33, 41, and instrumentation port 111 is similar to instrumentation port 29. The side arms are offset longitudinally along central arm 103 such that the passageways in side arms 101, 102 are not directly opposite the passageway in side arm 104 where they intersect the passageway in the central arm.

In the embodiment of FIG. 7, the hemostatic valve has two side arms on each side of a central arm 112. The side arms on one side of the central arm are designated by the reference numerals 113, 114, and the side arms on the other side are designated by the reference numerals 116, 117. An exit port 119 is provided at the distal end of the central arm, and access ports 121-124 are provided at the proximal ends of side arms 114, 116, 117 and central arm 112. An instrumentation port 126 is provided at the proximal end of side arm 113. Each of the access ports is separately sealed and similar to access ports 33, 41, and instrumentation port 126 is similar to instrumentation port 29. The side arms are offset longitudinally along central arm 112 such that the passageways in side arms 113, 114 are not directly opposite the passageways in side arms 116, 117 where they intersect the passageway in the central arm.

In the embodiment of FIG. 8, four side arms 131-134 are spaced radially in quadrature about a central arm 136. An exit port 137 is provided at the distal end of central arm 136 and access ports 141-144 are provided at the proximal ends of side arms 131-133 and central arm 136. An instrumentation port 146 is provided at the proximal end of side arm 134. Each of the access ports is separately sealed and similar to access ports 33, 41, and instrumentation port 146 is similar to instrumentation port 29. Side arms 141-144 are illustrated as intersecting the central arm in a common radial plane, but they can be offset longitudinally along the central arm so that none of the passageways are directly opposite each other at the intersections with the passageway in the central arm.

Operation and use of the embodiments of FIGS. 6-8 is generally similar to that of the other embodiments heretofore described, except that additional elements can be introduced through the additional access ports. Each of the access ports is separately sealed, and an element introduced through any of these ports can be moved without disturbing the other ports.

It is apparent from the foregoing that a new and improved apparatus for positioning a plurality of elongated elements in the cardiovascular system have been provided. While only certain presently preferred embodiments have been described in detail, as will be apparent to those familiar with the art, certain changes and modifications can be made without departing from the scope of the invention as defined by the following claims.

We claim:

1. In a hemostatic valve: an exit port adapted for connection to a guiding catheter or the like, an instrumentation port in fluid communication with the exit port, a first access port in communication with the exit port and adapted to receive a first elongated element which passes through the guiding catheter, means for sealing the first access port about the first elongated element, a second access port in communication with the exit port and adapted for receiving a second elongated element which passes through the guiding catheter and can be manipulated independently of the first element, and means for sealing the second access port about the second elongated element.

2. The hemostatic valve of claim 1 including means for rotatively connecting the guiding catheter to the exit port.

3. The hemostatic valve of claim 1 including at least one additional access port sealable independently of the other access ports for receiving at least one additional elongated element which passes through the guiding catheter and can be moved independently of the other elongated elements.

4. In apparatus for use in angioplasty: a valve having an exit port, an instrumention port in fluid communication with the exit port, and first and second separately sealable access ports; a guiding catheter having a luminal opening connected to the exit port; a first elongated element passing through the first access port and the luminal opening of the guiding catheter; and a second elongated element passing through the second access port and the luminal opening of the guiding catheter and being movable independently of the first element.

5. The apparatus of claim 4 wherein the first elongated element comprises a dilatation catheter.

6. The apparatus of claim 5 wherein the second elongated element comprises a guide wire.

7. The apparatus of claim 4 including at least one additional access port sealable independently of the other access ports, and an elongated element passing through each additional access port and the luminal opening of the guiding catheter and being movable independently of the other elongated elements.

8. In a hemostatic valve: a body having an exit port, a central arm aligned axially with the exit port and a pair of side arms intersecting the central arm at an angle; an instrumentation port formed in one of the side arms in fluid communcation with the exit port; a first access port formed in the central arm and communicating with the exit port for receiving a first elongated element which passes through the exit port; means for sealing the first access port about the first elongated element; a second access port formed in the second side arm for receiving a second elongated element which passes through the exit port and can be manipulated independently of the first elongated element; and means for sealing the second access port about the second elongated element.

9. The hemostatic valve of claim 8 wherein the means for sealing the access ports comprise end caps threadedly mounted on the central arm and the second side arm with openings through which the elongated elements can pass, and sealing glands compressed about the elongated elements by rotation of the end caps.

10. The hemostatic valve of claim 9 wherein each of the access ports includes an axial bore with a radially extending shoulder forming a seat for one of the sealing glands, and each of the end caps has an axially extending stem which extends into the bore and compresses the gland against the seat.

11. The hemostatic valve of claim 10 wherein the seat in each of the access ports is conically tapered.

12. The hemostatic valve of claim 8 including a rotary connector for attaching a guiding catheter to the exit port.

13. The hemostatic valve of claim 8 including at least one additional side arm which intersects the central arm, and a separately sealable access port formed in each additional side arm for receiving an elongated element which passes through the exit port and can be moved independently of the other elongated elements.

14. The hemostatic valve of claim 13 wherein the side arms lie in planes which extend radially from the central arm.

15. In a method of positioning elongated elements such as guide wires and dilatation catheters in the cardiovascular system of a patient, utilizing a hemostatic valve having an exit port and a pair of access ports, the steps of: connecting the proximal end of a guiding catheter having a luminal opening to the exit port; positioning the distal end of the guiding catheter in the cardiovascular system of the patient; inserting a first elongated element into the cardiovascular system through a first one of the access ports, the exit port and the luminal opening of the guiding catheter with the distal end portion of the elongated element extending beyond the distal end of the guiding catheter; forming a fluid-tight seal between the first elongated element and the first access port; introducing a second elongated element into the cardiovascular system through the second access port, the exit port and the luminal opening of the guiding catheter; said second elongated element being movable independently of the first elongated element; and forming a fluid-tight seal between the second elongated element and the second access port.

16. The method of claim 15 wherein the hemostatic valve has at least three access ports, an independently movable elongated element is introduced into the cardiovascular system through each of the access ports, and a fluid-tight seal is formed between each of the access ports and the elongated element passing through the same.

17. In a hemostatic valve: an exit port adapted for connection to a guiding catheter or the like, an instrumentation port in fluid communication with the exit port, at least three access ports in communication with the exit port and adapted to receive elongated elements which pass through the guiding catheter and can be moved independently of each other, and separate means for sealing each of the access ports independently of the other ports.

* * * * *